(12) United States Patent
Wang

(10) Patent No.: US 8,199,986 B2
(45) Date of Patent: Jun. 12, 2012

(54) VERTEBRA CENTER DETECTION APPARATUS USING SPINAL-CORD REGION DETECTION, METHOD AND RECORDING MEDIUM STORING A PROGRAM

(75) Inventor: Caihua Wang, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 661 days.

(21) Appl. No.: 12/367,252

(22) Filed: Feb. 6, 2009

(65) Prior Publication Data
US 2009/0202122 A1 Aug. 13, 2009

(30) Foreign Application Priority Data

Feb. 7, 2008 (JP) .................................. 2008/027145
Feb. 5, 2009 (JP) .................................. 2009/024455

(51) Int. Cl.
*G06K 9/00* (2006.01)
*A61B 5/103* (2006.01)

(52) U.S. Cl. .......................... 382/128; 382/131; 600/594
(58) Field of Classification Search ........................ None
See application file for complete search history.

(56) References Cited

U.S. PATENT DOCUMENTS

| | | | |
|---|---|---|---|
| 6,853,741 B1 * | 2/2005 | Ruth et al. ..................... | 382/132 |
| 7,137,958 B2 * | 11/2006 | Wada et al. .................... | 600/594 |
| 7,231,073 B2 | 6/2007 | Tanaka | |
| 2008/0044074 A1 * | 2/2008 | Jerebko et al. ................ | 382/128 |

* cited by examiner

*Primary Examiner* — Vinh Nguyen
(74) *Attorney, Agent, or Firm* — Birch, Stewart, Kolasch & Birch, LLP

(57) ABSTRACT

A plurality of medical images showing transverse cross-sections of vertebrae that have been imaged in advance are obtained. A spinal-cord region in at least one of the plurality of medical images is detected. A spinal-cord center-line based on a center point in the detected spinal-cord region is generated. A longitudinal cross-sectional image of the vertebrae is generated. Further, a center-line of the vertebrae is obtained based on a positional relationship between the spinal-cord center-line and the vertebrae.

8 Claims, 4 Drawing Sheets

VERTEBRA CENTER DETECTION APPARATUS USING SPINAL-CORD REGION DETECTION, METHOD AND RECORDING MEDIUM STORING A PROGRAM

BACKGROUND OF THE INVENTION

1. Field of the Invention

The present invention relates to processing for detecting a vertebra or vertebrae, and particularly to a vertebra center detection apparatus and method that is appropriate for automatically detection of the center of the vertebra or vertebrae in medical images. Further, the present invention relates to a recording medium stored therein a program for the apparatus and the method.

2. Description of the Related Art

Conventionally, automatic calculation of the center line of vertebrae based on a plurality of medical images that have been obtained by scanning a subject at a plurality of slice positions from the chest to the groins of the subject has been an essential technique in medical fields. Such an automatic calculation technique is indispensable to produce a vertebra CPR (Curved Planar Reconstruction) image to diagnose a compression fracture and to calculate the curvature of the vertebrae.

Therefore, processing for automatically detecting the center line of vertebrae in a plurality of medical images is performed by using a computer. For example, a technique for calculating the center line of the vertebrae by detecting the edge of the vertebrae in the medical images is proposed in U.S. Pat. No. 7,231,073.

However, the conventional techniques had problems that the vertebra detection performance (accuracy in detection of a vertebra or vertebrae) does not improve, because the shapes of structures in the medical images vary according to slice positions and an edge is generated by a structure in the vicinity of the vertebra. The shapes of the structures in the medical images vary, because the structures, such as ribs and clavicles, have different anatomical characteristics from each other.

Further, there has been a problem that when a subject has a lesion, such as osteoporosis and hyperostosis, if information about the edge of the structure is used alone, it is impossible to stably detect the vertebrae.

SUMMARY OF THE INVENTION

In view of the foregoing circumstances, it is an object of the present invention to provide a vertebra center detection apparatus and method that can improve the performance of detecting the center line of the vertebra or vertebrae and to provide a recording medium stored therein a program for the apparatus and the method.

A vertebra center detection apparatus according to the present invention is a vertebra center detection apparatus comprising:

an image obtainment unit that obtains a plurality of medical images showing transverse cross-sections of vertebrae that have been imaged in advance;

a spinal-cord region detection unit that detects a spinal-cord region in at least one of the plurality of medical images;

a spinal-cord center-line generation unit that generates a spinal-cord center-line based on a center point in the detected spinal-cord region; and a vertebra center-line calculation unit that generates a longitudinal cross-sectional image of the vertebrae, and obtains, based on a positional relationship between the spinal-cord center-line and the vertebrae, a center-line of the vertebrae.

The vertebra center detection apparatus according to the present invention may be a vertebra center detection apparatus, wherein the spinal-cord region detection unit detects a spinal-cord region in each of the plurality of medical images, and wherein the spinal-cord center-line generation unit generates a spinal-cord center-line based on center points in the plurality of spinal-cord regions that have been detected.

The "medical images" are axial images or the like, which are provided for diagnosis using images. For example, the medical images are radiographic images (radiographs), CT (computer tomography) images, MRI (magnetic resonance imaging) images, RI (radioisotope) images, PET (positron emission tomography) images and the like.

Further, the "center point (center points)" is a predetermined pixel that is present substantially at the center of the spinal-cord region. It is not necessary that the center point is located exactly at the center of the spinal-cord region. For example, the center point may be a point that is substantially equidistant from the circumference of the spinal-cord region or a point that is substantially equidistant from predetermined two ends or sides of the spinal-cord region. Alternatively, the center point may be the center of gravity or the like.

Further, the "spinal-cord region detection unit" detects the spinal-cord region in at least one of the plurality of medical images. For example, the spiral-cord region detection unit may set, based on a pixel of interest in the at least one of the plurality of medical images, a region in the vicinity of the pixel of interest (a region surrounding or including the pixel of interest), and judge whether the region in the vicinity of the pixel of interest is the spinal-cord region, using a classifier that has been obtained by using a machine learning method. The "classifier" may be obtained by using a so-called machine learning method. For example, a classifier obtained by so-called Boosting, particularly, by using AdaBoost learning algorithm may be used. The classifier may be obtained by setting, based on the pixel of interest, a region in the vicinity of the pixel of interest in each of a plurality of medical images, and by using a machine learning method, for example. Further, the classifier may calculate a classification value indicating the degree of certainty (reliability) of the judgment that the region in the vicinity of the pixel of interest is the spinal-cord region.

Further, the "spinal-cord center-line generation unit" calculates the spinal-cord center-line based on the center point in the detected spinal-cord region. For example, the spinal-cord center-line generation unit may judge that the pixel of interest, the classification value of the region in the vicinity of which is greater than or equal to a predetermined value, is the center point of the spiral-cord region.

The spinal-cord center-line generation unit may calculate the spinal-cord center-line based on a center point in a spinal-cord region in a single medical image. Alternatively, the spinal-cord center-line generation unit may calculate the spinal-cord center-line based on a center point in a spinal-cord region in each of a plurality of medical images.

Further, the "vertebra center-line calculation unit" may include a longitudinal cross-sectional image generation unit and a vertebra detection unit. The longitudinal cross-sectional image generation unit may extract, from each of the plurality of medical images, the brightness value of each pixel on a straight line in the respective medical images, a straight line passing through a predetermined point at which each of the plurality of medical images and the spinal-cord center-line intersect each other and a spine region but not passing through any part of a cardiac region (heart), and generate the longitudinal cross-sectional image using each of the straight lines including the pixels having the extracted brightness values.

Further, the vertebra detection unit may detect two trabecula lines having brightness values that are higher than or equal to a predetermined brightness value in the longitudinal cross-sectional image, and detect, as the vertebrae, a region including the spine region between the two trabecula lines.

The "vertebra detection unit" may shift the spinal-cord center-line in the longitudinal cross-sectional image so that the spinal-cord center-line becomes the same as each of the two trabecula lines by performing linear transformation on the spinal-cord center-line. When the vertebra detection unit shifts the spinal-cord center line to one of the two trabecula lines, the vertebra detection unit may calculate a first shift amount. When the vertebra detection unit shifts the spinal-cord center line to the other trabecula line, the vertebra detection unit may calculate a second shift amount. Further, the vertebra detection unit may calculate, based on the first shift amount and the second shift amount, the width of the vertebrae, and calculates the center line of the vertebrae based on the calculated width.

A method for detecting the center of vertebrae according to the present invention is a method for detecting the center of a vertebra or vertebrae, the method comprising the steps of:

obtaining a plurality of medical images showing transverse cross-sections of vertebrae that have been imaged in advance;

detecting a spinal-cord region in at least one of the plurality of medical images;

generating a spinal-cord center-line based on a center point in the detected spinal-cord region;

generating a longitudinal cross-sectional image of the vertebrae; and obtaining, based on a positional relationship between the spinal-cord center-line and the vertebrae, a center-line of the vertebrae.

Further, a computer-readable recording medium stored therein a program for causing a computer to execute a method for detecting the center of vertebrae according to the present invention is a computer-readable recording medium stored therein a program for causing a computer to execute a method for detecting the center of vertebrae, the program comprising the functions of:

obtaining a plurality of medical images showing transverse cross-sections of vertebrae that have been imaged in advance;

detecting a spinal-cord region in at least one of the plurality of medical images;

generating a spinal-cord center-line based on a center point in the detected spinal-cord region;

generating a longitudinal cross-sectional image of the vertebrae; and obtaining, based on a positional relationship between the spinal-cord center-line and the vertebrae, a center-line of the vertebrae.

According to the vertebra center detection apparatus and method of the present invention and the recording medium stored therein a program for the apparatus and the method of the present invention, a spinal-cord region is detected in at least one of a plurality of medical images. Further, a spinal-cord center-line is generated based on a center point in the detected spinal-cord region. Further, a longitudinal cross-sectional image of the vertebrae is generated. Further, the center-line of the vertebrae is obtained based on a positional relationship between the spinal-cord center-line and the vertebrae. Therefore, it is possible to stably detect the center line of the vertebrae.

Further, when the brightness value of each pixel on a straight line in each of medical images, the straight line passing through the center point and a spine region but not passing through any part of a cardiac region, is extracted from each of the plurality of medical images, and the longitudinal cross-sectional image is generated using each of the straight lines including the pixels having the extracted brightness values, it is possible to exclude irregular pixels, the irregularity of which is caused by blood vessels that are present in the vicinity of the cardiac region. Hence, it is possible to stably produce the longitudinal cross-sectional image.

Further, those who are skilled in the art would know that computer readable media are not limited to any specific type of device, and include, but are not limited to: floppy disks, CD's, RAM's, ROM's, hard disks, magnetic tapes, and internet downloads, in which computer instructions can be stored and/or transmitted. Transmission of the computer instructions through a network or through wireless transmission means is also within the scope of this invention. Additionally, computer instructions include, but are not limited to: source, object and executable code, and can be in any language including higher level languages, assembly language, and machine language.

DESCRIPTION OF THE PREFERRED EMBODIMENTS

Hereinafter, an embodiment of a vertebra center detection apparatus according to the present invention will be described with reference to the drawings.

Figure 1:
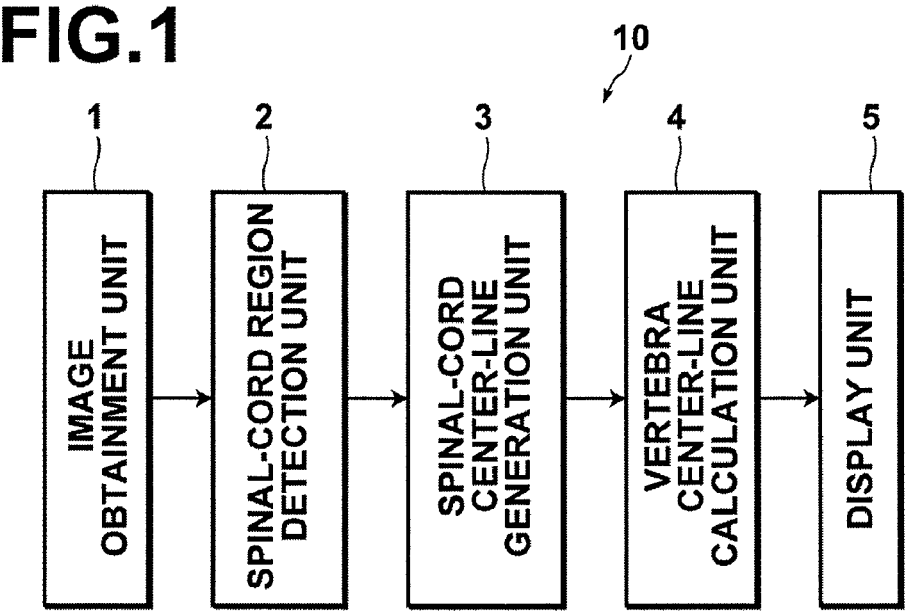
FIG. 1 is a block diagram illustrating the function of a vertebra center detection apparatus.

FIG. 1 is a block diagram illustrating an embodiment of a vertebra center detection apparatus 10 of the present invention.

The configuration of the vertebra center detection apparatus 10, as illustrated in FIG. 1, is realized by causing a computer (for example, a personal computer or the like) to execute a vertebra center detection program installed in an auxiliary recording apparatus (supplementary storage apparatus) (not illustrated). Further, the vertebra center detection program may be stored in an information recording medium, such as a CD-ROM (compact disk read-only memory), or distributed through a network, such as the Internet, to be installed in a computer.

The vertebra center detection apparatus 10 automatically calculates a vertebra center-line in medical images obtained as CT images, for example. The vertebra center detection apparatus 10 includes an image obtainment unit 1, a spinal-cord region detection unit 2, a spinal-cord center-line generation unit 3, a vertebra center-line calculation unit 4, a display unit 5, and the like.

Figure 3:
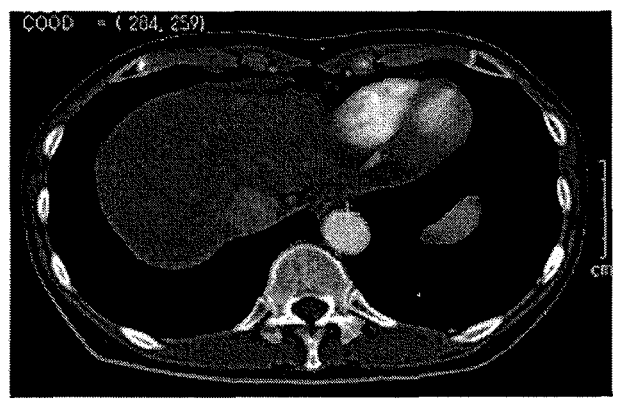
FIG. 3 is a diagram illustrating an example of an axial image.

The image obtainment unit 1 obtains medical images that have been obtained as CT images, as illustrated in FIG. 3, for example. It is not necessary that the medical images are the CT images. The image obtainment unit 1 may obtain MRI images, RI images, PET image, X-ray (radiographic) images and the like.

The spinal-cord region detection unit 2 detects a spinal-cord region in each of a plurality of medical images. The spinal-cord region detection unit 2 sets, based on a pixel of interest in each of the plurality of medical images, a region in the vicinity of the pixel of interest, and judges whether the region in the vicinity of the pixel of interest is the spinal-cord region, using a classifier that has been obtained by using a machine learning method.

The spinal-cord center-line generation unit 3 generates a spinal-cord center-line in a longitudinal cross-sectional image of the vertebrae based on center points in the plurality of spinal-cord regions that have been detected by the spinal-cord region detection unit 2. Further, when the classifier used by the spinal-cord region detection unit 2 calculates a classification value indicating the degree of certainty (reliability) of the judgment that the region in the vicinity of the pixel of interest is the spinal-cord region, the spinal-cord center-line generation unit 3 judges that the pixel of interest, the classification value of the region in the vicinity of which is greater than or equal to a predetermined value, is the center point of the spiral-cord region.

The vertebra center-line calculation unit 4 obtains, based on a positional relationship between the spinal-cord center-line generated by the spinal-cord center-line generation unit 3 and the vertebrae, a center line of the vertebrae.

Figure 4:
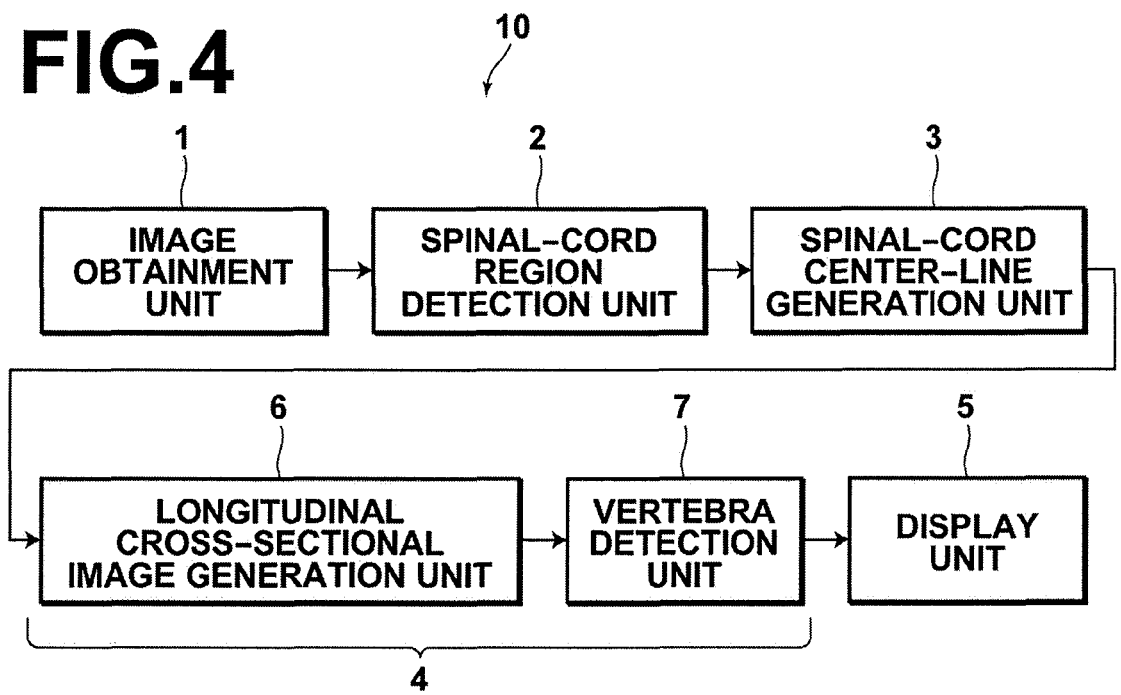
FIG. 4 is a block diagram illustrating the function of a vertebra center-line calculation unit in the vertebra center detection apparatus.

FIG. 4 is a block diagram illustrating the configuration of the vertebra center-line calculation unit 4 in an image processing apparatus. As illustrated in FIG. 4, the vertebra center-line calculation unit 4 includes a longitudinal cross-sectional image generation unit 6 and a vertebra detection unit 7.

Figure 8:
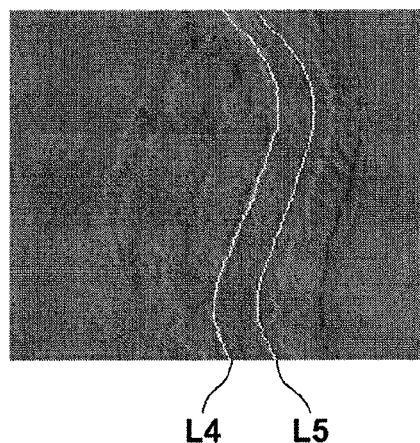
FIG. 8 is a diagram showing the boundary lines of vertebrae.

The longitudinal cross-sectional image generation unit 6 extracts, from each of medical images, the brightness value of each pixel on a straight line in the respective medical images, the straight line passing through the center point in the spinal-cord region detected by the spinal-cord region detection unit 2 and a spine region but not passing through any part of a cardiac region. Further, the longitudinal cross-sectional image generation unit 6 generates the longitudinal cross-sectional image, for example as illustrated in FIG. 8, using each of the straight lines including the pixels having the extracted brightness values.

Further, the longitudinal cross-sectional image generation unit 6 may extract, from each of the plurality of medical images, the brightness value of each pixel on a straight line in the respective medical images, the straight line passing through a predetermined point at which each of the plurality of medical images and the spinal-cord center-line intersect each other and a spine region but not passing through any part of a cardiac region, and generate the longitudinal cross-sectional image using each of the straight lines including the pixels having the extracted brightness values.

The vertebra detection unit 7 detects two trabecula lines having brightness values that are higher than or equal to a predetermined brightness value in the longitudinal cross-sectional image generated by the longitudinal cross-sectional image generation unit 6, and detects, as the vertebrae, a region including the spine region between the two trabecula lines.

The display unit 5 is a monitor, a CRT (cathode-ray tube) display or the like for displaying medical images.

Next, processing in the embodiment of the vertebra center detection apparatus 10, which is configured as described above, will be described.

Figure 2:
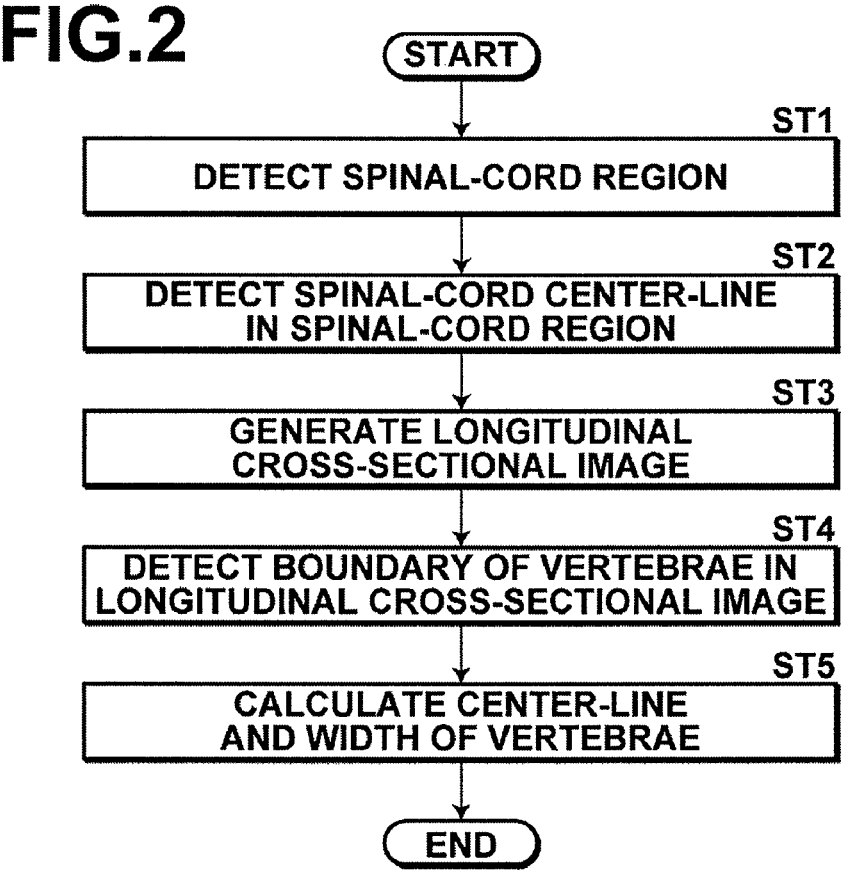
FIG. 2 is a flow chart of processing in an embodiment of the present invention.

FIG. 2 is a flow chart of processing by a vertebra center detection apparatus. As illustrated in FIG. 2, first, the spinal-cord region detection unit 2 detects a spinal-cord region in each of a plurality of medical images obtained by the image obtainment unit 1 (step ST1). For example, FIG. 3 is a typical CT image of the spinal cord of a subject of medical images (axial images) that are constituted of slice images obtained at a plurality of slice positions when the subject is transversely sliced at the plurality of slice positions from the chest to the groin (inguen) region thereof. Since the spinal-cord region generally has a clear pattern, it is possible to stably detect the spinal-cord region in the medical image by using an image detection technique.

As a method for detecting the spinal-cord region, a machine learning method based on Adaboost, which is a technique for obtaining an integrated-learning machine, may be used.

Figure 5:
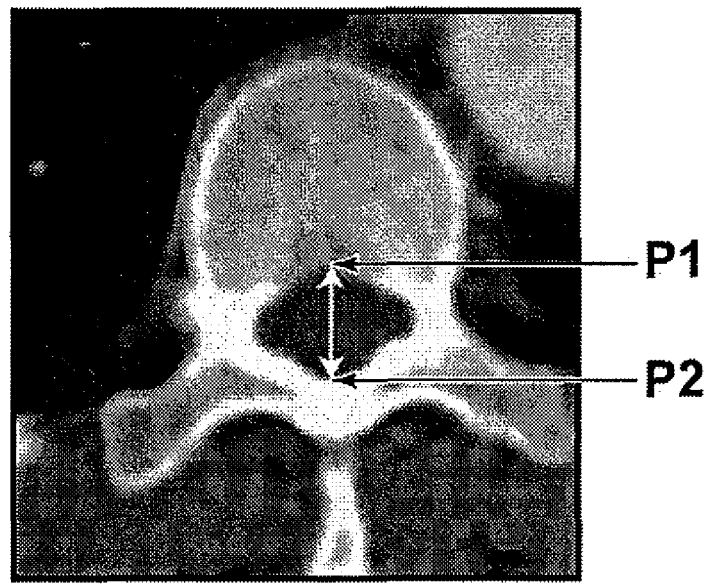
FIG. 5 is a diagram illustrating an example of a partial axial image in the vicinity of a vertebra.

The method for detecting the spinal-cord region may be used as a method for detecting the spinal-cord region in the vertebra center detection apparatus according to the present invention. The spinal-cord region may be followed by using a known technique, such as a feature point detection technique, or by using a machine learning method based on Adaboost, which is a technique for obtaining an integrated-learning machine. The integrated-learning machine is obtained by sequentially updating weight on learning data at the time of re-sampling and by further weighting the obtained learning machine at the end. For example, as illustrated in FIG. 5, two points, upper point P1 and lower point P2, are specified in the spinal-cord region of a learning sample image. Further, a midpoint between the two points is set as the center of a region of interest, and the region of interest is set, with respect to the set center, in a quadrilateral area (square area) having a side that is twice the distance between the two specified points. Quadrilateral areas are extracted from CT images of various patients at various positions (thoracic vertebra, lumbar vertebra or the like), and the sizes of the quadrilateral areas are normalized so that they have a uniform size. The regions of interest of these images are used as positive learning samples.

Next, quadrilateral areas having various sizes are randomly extracted from areas of the CT images, the areas away from the specified regions (regions of interest). Further, the sizes of the quadrilateral areas are changed so that they have a uniform size, and the quadrilateral regions are used as negative learning samples.

Figure 6:
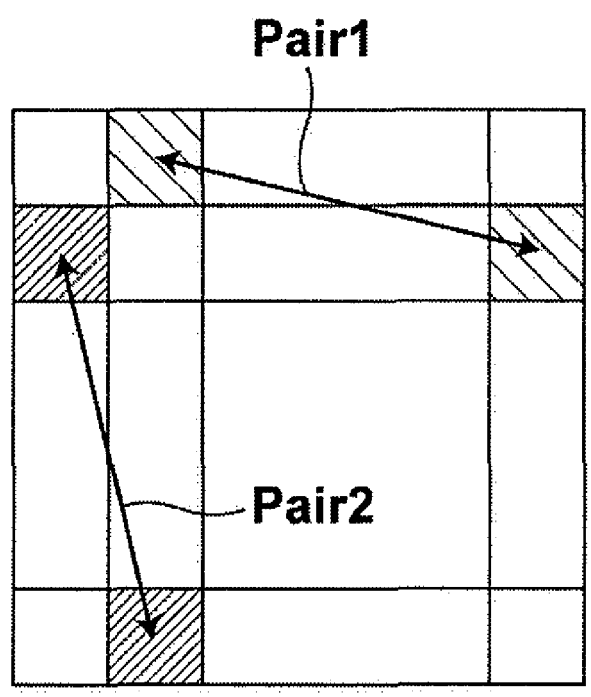
FIG. 6 is a conceptual diagram illustrating an example of a feature value used in AdaBoost processing.

Next, machine learning is performed on the positive learning samples and the negative learning samples to obtain a classifier for distinguishing a positive pattern and a negative pattern from each other. For example, as illustrated in FIG. 6, a combination of n-number of pixel pairs that have been randomly selected is used as a feature value, and the classifier is obtained by using a machine learning method based on Adaboost.

When the spinal-cord region is detected, the medical image is scanned, and quadrilateral areas that have various sizes are extracted in such a manner that the pixels of interest become the centers of the quadrilateral areas. Then, the feature value is calculated as illustrated in FIG. 6.

The obtained feature values are input to the classifier that has been obtained by learning, and classification values are obtained. Then, the highest classification value is set as the score of the pixel of interest. A position (pixel) that has the highest classification value is detected in the medical image, and the position (pixel) is set as the center of the spinal-cord region.

Further, as a method for detecting the spinal-cord region, methods, such as a known template matching method (for example, a method disclosed in Japanese Unexamined Patent Publication No. 2002-109548) and a demarcation method using a ring model (for example, a method disclosed in Japanese Unexamined Patent Publication No. 2007-111533), may be used to detect the spinal-cord region in the image processing apparatus of the present invention.

Next, the spinal-cord center-line generation unit 3 generates the center line of the spinal cord based on the center points of the spinal cord regions (step ST2). A predetermined pixel that is located substantially at the center of the spinal-cord region is set as the center point. It is not necessary that the center point is located at the exact center of the spinal-cord region. The center point may be a point that is substantially equidistant from the circumference (boundary or periphery) of the spinal-cord region or a point that is substantially equidistant from predetermined two ends or sides of the spinal-cord region. Alternatively, the center of gravity may be set as the center point.

Specifically, a spinal-cord center line that is a smooth three-dimensional line is obtained based on the center of the spinal-cord region in each of a plurality of medical images obtained in the previous step. As a method for calculating the center line of the spinal cord, a method (for example, a method disclosed in Japanese Unexamined Patent Publication No. 6(1994)-189934) in which a polygonal line or a curved line (curve) is fitted onto the obtained center points of the spinal-cord regions may be used. Alternatively, RANSAC (random sample consensus) method (for example, a method disclosed in M. A. Fischler and R. C. Bolles, "Random Sample Consensus: A Paradigm for Model Fitting with Applications to Image Analysis and Automated Cartography", Comm. of the ACM 24, pp. 381-395, 1981) may be used. In the RANSAC method, a few samples are randomly extracted and a least square method is applied thereto.

The spinal-cord center-line generation unit 3 may generate the spinal-cord center-line in such a manner that the spinal-cord center-line is slightly shifted (away) from at least one of the center points in the spinal-cord regions of the plurality of medical images by using the aforementioned methods.

Further, when the spinal-cord center-line generation unit 3 sets the center points based on the detected spinal-cord regions, the spinal-cord center-line generation unit 3 may use obtained classification values (values representing the degrees of certainty of judgment that the regions are classified as spinal-cord regions, in other words, values corresponding to the degrees of presence of spinal-cord region characteristics in the patterns). In that case, center points only in spinal-cord regions, the classification values of which exceed a threshold value, are selected. Further, a smooth three-dimensional curve of the spinal-cord region is generated by using the aforementioned technique for calculating the spinal-cord center line.

Further, when the spinal-cord center-line is calculated, the classification value may be used as a weighting factor (coefficient) of the center point of the spinal-cord region.

Figure 7:
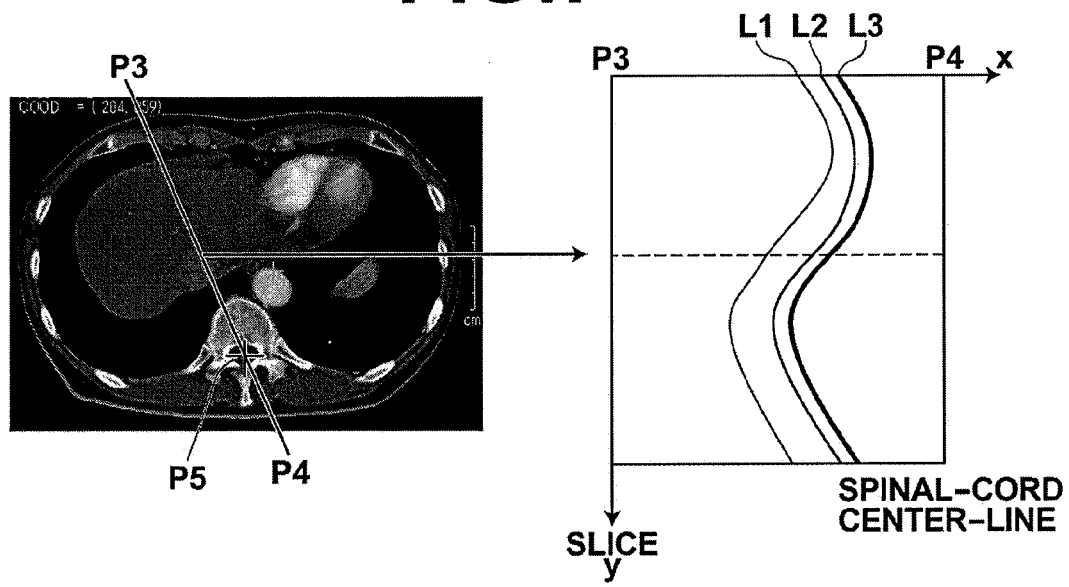
FIG. 7 is a diagram illustrating an example of an axial image and a longitudinal cross-sectional image along a spinal-cord center line.

Next, the longitudinal cross-sectional image generation unit 6 generates a longitudinal cross-sectional image (step ST3). Specifically, the center line of the spine is calculated based on the spinal-cord center-line calculated by using the method for calculating the spinal-cord center-line, as described above. To calculate the center line of the spine, first, the center of the spinal-cord region obtained in each of the medical images is used. As illustrated in FIG. 7, the center point is used as the base point, and the brightness value of each pixel on a straight line that is inclined counterclockwise from the Y-axis by α degrees is extracted from each of the medical images. Further, a longitudinal cross-sectional image is generated based on each of the straight lines having the extracted brightness values. The aforementioned straight lines form the longitudinal cross-sectional image. Meanwhile, the cardiac region (heart) includes many blood vessels and the like, and it does not have a stable pattern. Therefore, the aforementioned straight line may be set in such a manner that the line goes through the center point and the spine region, but does not go through any part of the cardiac region.

The vertebra detection unit 7 detects the boundary (edge) of the vertebra in the longitudinal cross-sectional image (step ST4). Specifically, the spinal-cord center line in the longitudinal cross-section image is a single curved line. Further, as a spine region, two trabecula lines that have high CT values and a cancellous bone region between the two trabecula lines, the cancellous bone region having low CT values, appear on the left side of the spinal-cord center line.

The vertebra detection unit 7 calculates the center line of the vertebrae and the width thereof (step ST5). Specifically, the center line of the vertebrae is calculated by using the spinal-cord center line, which is curved line L3 in FIG. 7. First, a difference in the direction of the X axis is obtained in the longitudinal cross-sectional image illustrated in FIG. 7. A large positive difference value is obtained at the ventral-side edge portion of the spine region, and a large negative difference value is obtained at the dorsal-side edge portion of the spine region.

Center point P5 illustrated in FIG. 7 may be a predetermined point at which the spinal-cord center-line generated by the spinal-cord center-line generation unit 3, as described above, and a medical image intersect each other. Alternatively, the center point P5 may be a predetermined point at which the spinal-cord center-line generated by applying a spinal-cord center-line model that will be described later and a medical image intersect each other.

The vertebra detection unit 7 performs linear transformation on the spinal-cord center line L3 to fit the spinal-cord center line L3 onto the dorsal-side edge line L2 of the spine region. For that purpose, the vertebra detection unit 7 calculates linear transformation coefficients a and b using Formula (1):

$$\sum_{i=1}^{N} g_x(ay_i + x_i + b, y_i), \tag{1}$$

and calculates the dorsal-side edge line L5 of the spine region.

Further, with respect to the ventral-side edge curved line L1, an edge curved line L4 is obtained by using a similar method.

Further, the method for performing fitting is not limited to the method using the above formula. The curved lines L4 and L5 may be directly obtained based on the gradients of the brightness values in the longitudinal cross-sectional image.

The curved lines L4 and L5, which have been calculated as illustrated in FIG. 8, form left and right boundary lines (boundaries) of the vertebra including the spine region. Further, it is possible to calculate, based on the calculated left/right boundary lines, the center line of the vertebra, which passes between the boundary lines of the vertebra, and a width between the boundary lines of the vertebra.

As described above, according to an embodiment of the present invention, it is possible to accurately calculate the center of the vertebra (or the center line of the vertebrae) based on the positional relationship thereof with the spinal-cord center line in the medical images.

In the aforementioned embodiment, the vertebra center-line calculation unit 4 obtains the center line of the vertebrae based on the positional relationship between the spinal-cord center line generated by the spinal-cord center-line generation unit 3 and the vertebrae. Here, processing for calculating the vertebra center line, using a voxel image in which medical images are superposed one on another, will be described.

When the center point P5 of the spinal-cord region detected by the spinal-cord region detection unit 2 and the center line of the voxel image are defined as in Formula (2):

$$(X_k^c, Y_k^c, Z_k^c), k=1, \Lambda, N. \ (N: \text{SLICE NUMBER}) \quad (2),$$

the longitudinal cross-sectional image generation unit 6 can generate a new longitudinal cross-sectional image by cutting the voxel image at a slice plane that connects points P3 and P4 in FIG. 7, the image being as represented by Formula (3):

$$P_k^s(\lambda) = \begin{pmatrix} X_k^s(\lambda) \\ Y_k^s(\lambda) \\ Z_k^s(\lambda) \end{pmatrix} = \begin{pmatrix} X_k^c \\ Y_k^c \\ Z_k^c \end{pmatrix} + \lambda \begin{pmatrix} \cos(\theta) \\ \sin(\theta) \\ 0 \end{pmatrix}. \quad (3)$$

In Formula (3), θ represents an inclination angle (gradient) of the cross-sectional plane that connect points P3 and P4 in FIG. 7. Further, in Formula (3), λ represents a position on the cross-sectional plane. The range of the position (the range of λ) is determined by the range of the frame of the medical image.

The vertebra detection unit 7 detects two trabecula lines that have brightness values greater than or equal to a predetermined brightness value in the longitudinal cross-sectional image newly generated by the longitudinal cross-sectional image generation unit 6. Further, the vertebra detection unit 7 detects, as the vertebra or vertebrae, a region including the spine region between the two trabecula lines.

To obtain the two trabecula lines, the vertebra detection unit 7 may obtain the edge of the new longitudinal cross-sectional image by using Formula (4):

$$g'(P_k^s(\lambda)) = \frac{dg(P_k^s(\lambda))}{d\lambda} \approx \frac{g(P_k^s(\lambda + \Delta)) - g(P_k^s(\lambda))}{\Delta}. \quad (4)$$

The value of Δ is a small value, which normally corresponds to one pixel. However, the value of Δ is not limited to such a value.

Further, the vertebra detection unit 7 can perform, based on the edge obtained by using Formula (4), fitting onto the dorsal-side wall of the vertebrae by using Formula (5):

$$\sum_{k=1}^{N} g'(P_k^s(aZ_k^c + b)) \to \min. \quad (5)$$

Further, when the vertebra detection unit 7 uses Formula (6):

$$\vec{P}_k^s(\lambda) = \begin{pmatrix} X_k^c \\ Y_k^c \\ Z_k^c \end{pmatrix} + (\tilde{a}Z_k^c + \tilde{b}) \begin{pmatrix} \cos(\theta) \\ \sin(\theta) \\ 0 \end{pmatrix}, \quad (6)$$

if the optimum parameter obtained by minimization is $(\tilde{a}, \tilde{b})$, the vertebra detection unit 7 can obtain curved line L5, which is the dorsal-side edge line of the vertebrae.

Further, the vertebra detection unit 7 may obtain the ventral-side edge curved line L4 by using a similar method.

The curved lines L4 and L5, which are calculated as illustrated in FIG. 8, are left and right boundary lines of the vertebrae including the spine region. Further, it is possible to calculate, based on the calculated left/right boundary lines, the center line of the vertebrae and a width between the boundary lines of the vertebrae.

As described above, according to an embodiment of the present invention, it is possible to accurately calculate the center of the vertebra or vertebrae based on the positional relationship between the center line of the spinal cord and the center of the vertebra or vertebrae by using a voxel image.

As described above, the vertebra center detection apparatus 10 of the present invention includes the image obtainment unit 1, the spinal-cord region detection unit 2, the spinal-cord center-line generation unit 3 and the vertebra center-line calculation unit 4. The image obtainment unit 1 obtains a plurality of medical images showing transverse cross-sections of vertebrae that have been imaged in advance. The spinal-cord region detection unit 2 detects a spinal-cord region in at least one of the plurality of medical images. The spinal-cord center-line generation unit 3 generates a spinal-cord center-line based on a center point in the detected spinal-cord region. The vertebra center-line calculation unit 4 generates a longitudinal cross-sectional image of the vertebrae, and obtains, based on a positional relationship between the spinal-cord center-line and the vertebrae, a center-line of the vertebrae.

The spinal-cord center-line generation unit 3 generates the spinal-cord center-line, based on center points in a plurality of spinal-cord regions detected by the spinal-cord region detection unit 2, in the longitudinal cross-sectional image of the vertebrae. Here, it is not necessary that the spinal-cord center-line generation unit 3 uses the center points in the plurality of spinal-cord regions detected by the spinal-cord region detection unit 2. The spinal-cord center-line generation unit 3 may generate the spinal-cord center-line based on a center point in the spinal-cord region of one of the medical images that has been detected by the spinal-cord region detection unit 2.

Specifically, the spinal-cord center-line generation unit 3 calculates a center point in a spinal-cord region of a medical image representing a subject at a predetermined position of height thereof (for example, a position in the vicinity of the abdomen of the subject or a position in the vicinity of the chest of the subject with respect to Z axis). Further, the spinal-cord center-line generation unit 3 applies an arbitrary spinal-cord center-line model based on the center point to generate the spinal-cord center-line. The spinal-cord center-line model is the average form of spinal-cord center-lines of humans, and stored in a database of the vertebra center detection apparatus.

Further, the longitudinal cross-sectional image generation unit 6 may obtain position information about the cardiac region from the database to set a straight line that does not pass any part of the cardiac region.

Further, the longitudinal cross-sectional image generation unit 6 may include a predetermined heart detection program. Further, the longitudinal cross-sectional image generation unit 6 may calculate the position of the heart by using the heart detection program, and set a straight line for generating the longitudinal cross-sectional image.

What is claimed is:

1. A vertebra center detection apparatus comprising:
   an image obtainment unit that obtains a plurality of medical images showing transverse cross-sections of vertebrae that have been imaged in advance;
   a spinal-cord region detection unit that detects a spinal-cord region in at least one of the plurality of medical images;
   a spinal-cord center-line generation unit that generates a spinal-cord center-line based on a center point in the detected spinal-cord region; and
   a vertebra center-line calculation unit that generates a longitudinal cross-sectional image of the vertebrae, and obtains, based on a positional relationship between the spinal-cord center-line and the vertebrae, a center-line of the vertebrae.

2. A vertebra center detection apparatus, as defined in claim 1, wherein the spinal-cord region detection unit detects a spinal-cord region in each of the plurality of medical images, and wherein the spinal-cord center-line generation unit generates a spinal-cord center-line based on center points in the plurality of spinal-cord regions that have been detected.

3. A vertebra center detection apparatus, as defined in claim 1, wherein the spiral-cord region detection unit sets, based on a pixel of interest in each of the plurality of medical images, a region in the vicinity of the pixel of interest, and judges whether the region in the vicinity of the pixel of interest is the spinal-cord region, using a classifier capable of distinguishing a spinal-cord region from a non-spinal-cord region,
   wherein said classifier is obtained by a machine learning method for learning a criterion for distinguishing a spinal-cord region and a non-spinal-cord region from each other by using
   positive learning samples, each representing a spinal-cord region, and
   negative learning samples, each representing a non-spinal-cord region.

4. A vertebra center detection apparatus, as defined in claim 3, wherein the classifier calculates a classification value indicating the degree of certainty of the judgment that the region in the vicinity of the pixel of interest is the spinal-cord region, and wherein the spinal-cord center-line generation unit judges that the pixel of interest, the classification value of the region in the vicinity of which is greater than or equal to a predetermined value, is the center point of the spinal-cord region.

5. A vertebra center detection apparatus, as defined in claim 1, wherein the vertebra center-line calculation unit includes a longitudinal cross-sectional image generation unit and a vertebra detection unit, wherein the longitudinal cross-sectional image generation unit extracts, from each of the plurality of medical images, the brightness value of each pixel on a straight line in the respective medical images, the straight line passing through a predetermined point at which each of the plurality of medical images and the spinal-cord center-line intersect each other and a spine region but not passing through any part of a cardiac region, and generates the longitudinal cross-sectional image using each of the straight lines including the pixels having the extracted brightness values, and wherein the vertebra detection unit detects two trabecula lines having brightness values that are higher than or equal to a predetermined brightness value in the longitudinal cross-sectional image, and detects, as the vertebrae, a region including the spine region between the two trabecula lines.

6. A vertebra center detection apparatus, as defined in claim 5, wherein the vertebra detection unit shifts the spinal-cord center-line in the longitudinal cross-sectional image so that the spinal-cord center-line becomes the same as each of the two trabecula lines by performing linear transformation on the spinal-cord center-line, and wherein when the vertebra detection unit shifts the spinal-cord center line to one of the two trabecula lines, the vertebra detection unit calculates a first shift amount, and wherein when the vertebra detection unit shifts the spinal-cord center line to the other trabecula line, the vertebra detection unit calculates a second shift amount, and wherein the vertebra detection unit calculates, based on the first shift amount and the second shift amount, the width of the vertebrae, and calculates the center line of the vertebrae based on the calculated width.

7. A method for detecting the center of vertebrae, the method comprising the steps of:
   obtaining a plurality of medical images showing transverse cross-sections of vertebrae that have been imaged in advance;
   detecting a spinal-cord region in at least one of the plurality of medical images;
   generating a spinal-cord center-line based on a center point in the detected spinal-cord region:
   generating a longitudinal cross-sectional image of the vertebrae; and
   obtaining, based on a positional relationship between the spinal-cord center-line and the vertebrae, a center-line of the vertebrae.

8. A non-transitory computer-readable recording medium containing a program that includes executable instructions, wherein the instructions cause a computer to:
   obtain a plurality of medical images showing transverse cross-sections of vertebrae that have been imaged in advance;
   detect a spinal-cord region in at least one of the plurality of medical images;
   generate a spinal-cord center-line based on a center point in the detected spinal-cord region;
   generate a longitudinal cross-sectional image of the vertebrae; and
   obtain, based on a positional relationship between the spinal-cord center-line and the vertebrae, a center-line of the vertebrae,
   thereby executing a method for detecting the center of vertebrae.

* * * * *